United States Patent [19]

Hagemann et al.

[11] Patent Number: 4,549,994

[45] Date of Patent: Oct. 29, 1985

[54] PREPARATION OF NEW FLUOROPIVALIC ACID FLUORIDES

[75] Inventors: Hermann Hagemann, Leverkusen; Erich Klauke, Odenthal; Ernst Kysela, Bergisch Gladbach, all of Fed. Rep. of Germany

[73] Assignee: Bayer Aktiengesellschaft, Leverkusen, Fed. Rep. of Germany

[21] Appl. No.: 630,490

[22] Filed: Jul. 13, 1984

[30] Foreign Application Priority Data

Jul. 26, 1983 [DE] Fed. Rep. of Germany ....... 3326875

[51] Int. Cl.$^4$ ............................................. C07C 53/50
[52] U.S. Cl. .................................. 260/544 F; 560/161
[58] Field of Search ..................................... 260/544 F

[56] References Cited

U.S. PATENT DOCUMENTS 3,414,612 12/1966 Tan et al. ..................... 260/544 K
3,725,475 4/1973 Paucksch et al. ............... 260/544 F

*Primary Examiner*—Natalie Trousof
*Assistant Examiner*—L. Hendriksen
*Attorney, Agent, or Firm*—Sprung, Horn, Kramer & Woods

[57] ABSTRACT

A process for the preparation of a compound according to claim 1, comprising reacting a compound of the formula

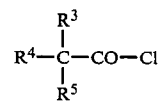

in which $R^3$, $R^4$ and $R^5$ each independently is $CH_3$ or $CH_2Cl$, at least one of the radicals $R^3$, $R^4$ and $R^5$ being $CH_2Cl$, with a metal fluoride at elevated temperature. The products are new and useful as intermediates for making other compounds, especially carbamate insecticide synergists.

2 Claims, No Drawings

PREPARATION OF NEW FLUOROPIVALIC ACID FLUORIDES

The invention relates to new fluoropivalic acid fluorides and a process for their preparation. The new fluoropivalic acid fluorides can be used as intermediates in wide fields of organic chemistry for synthesis purposes, the fields of pharmaceuticals, plant protection agents, dyestuffs, plastics and plastics auxiliaries being mentioned as examples. The new compounds can be particularly advantageously used for the synthesis of synergistic agents in the field of insecticides.

The new fluoropivalic acid fluorides of the general formula (I)

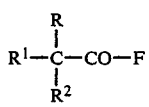

in which R, $R^1$ and $R^2$ independently of one another represent $CH_3$ or $CH_2F$, at least one of the radicals R, $R^1$ and $R^2$ denoting $CH_2F$, have now been found.

It has furthermore been found that the fluoropivalic acid fluorides of the general formula (I)

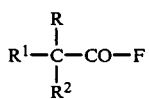

in which R, $R^1$ and $R^2$ independently of one another denote $CH_3$ or $CH_2F$, at least one of the radicals R, $R^1$ and $R^2$ denoting $CH_2F$, are obtained when corresponding chloropivalic acid chlorides of the general formula (II)

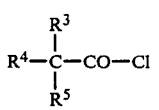

in which $R^3$, $R^4$ and $R^5$ independently of one another represent $CH_3$ or $CH_2Cl$, at least one of the radicals $R^3$, $R^4$ and $R^5$ denoting $CH_2Cl$, are reacted with metal fluorides at elevated temperatures, if appropriate in the presence of a solvent, and the compounds of the formula (I) are isolated, and if appropriate purified, by customary methods.

Compounds to be used according to the invention as starting substances of the general formula (II) are known and can be prepared by generally known processes and methods from the particular carboxylic acids.

It is to be regarded as decidedly surprising that the replacement of chlorine by fluorine in the neopentyl structure which is known to be particularly slow to react proceeds in such a smooth reaction and in a good yield in the case of the chloropivaloyl chlorides in the course of the process according to the invention, since, for example, dichloropinacolin can be converted into the corresponding difluoropinacolin with a maximum yield of only 20% under corresponding conditions.

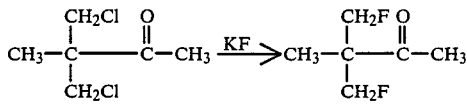

If, for example, dichloropivaloyl chloride is reacted with potassium fluoride, the process according to the invention can be illustrated by the following equation:

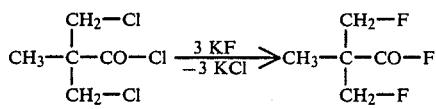

The alkali metal fluorides, such as sodium fluoride and potassium fluoride (particularly preferably potassium fluoride) are preferably used as metal fluorides in the process according to the invention.

At least as many moles of metal fluoride, that is to say, for example, potassium fluoride, as there are chlorine atoms to be replaced by fluorine atoms are used per mole of the starting compounds of the general formula (II), the acid chloride chlorine atom also being taken into consideration. Thus, the amount of metal fluoride, for example potassium fluoride, used is at least 2 moles for the reaction of monochloropivalic acid chloride, at least 3 moles for the reaction of dichloropivalic acid chloride and at least 4 moles for the reaction of trichloropivalic acid chloride. It may be advantageous to use the metal fluoride (for example potassium fluoride) in an excess of 5 to 15 mole %, preferably 8 to 12 mole %, per chlorine atom to be replaced.

The reaction can be carried out under normal pressure or under increased pressure. If appropriate, the reaction is carried out under an inert gas, such as nitrogen or helium.

The process according to the invention is carried out at elevated temperatures, preferably between 100 and 300° C. and particularly preferably between 130° and 250° C.

Possible solvents are all the organic solvents which are inert in the reaction.

These include, in particular, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycoldimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methylpyrrolidone, and dimethylsulphoxide, tetramethylene sulphone and hexamethylphosphoric acid triamide, and mixtures of these solvents. Tetramethylene sulphone (optionally as a mixture with one of the abovementioned solvents) is particularly preferably used.

As already mentioned above, the new compounds of the general formula (I) can be used for a large number of chemical syntheses.

Thus, the compounds of the formula (I) can be converted into the isocyanates in a known manner (compare, for example, Methoden der organischen Chemie (Methods of organic chemistry), Houben-Weyl, Volume IX/1 (1957), pages 867-872, Thieme-Verlag, Stuttgart), and with propargyl alcohol, these isocyanates give carbamic acid esters, which, surprisingly, exhibit a powerful synergistic action when mixed with arthropodicidal active compounds and thus can be used as agents for combating pests, in particular in insecticides.

To prepare the isocyanates, the fluoropivaloyl fluorides are reacted, for example, in a solution in acetone with approximately molar amounts of sodium azide in aqueous solution at about 0° to 20° C. The mixture is then extracted with toluene, the toluene phase is separated off and dried with sodium sulphate and the toluene solution is heated to the boiling point. The isocyanate formed can be reacted directly in the toluene solution or isolated by distillation.

The isocyanates are reacted with propargyl alcohol by generally customary methods, for example in molar amounts with the addition of catalytic amounts of diazobicyclooctane at room temperature.

The preparation of the carbamic acid esters can be illustrated by the following equation:

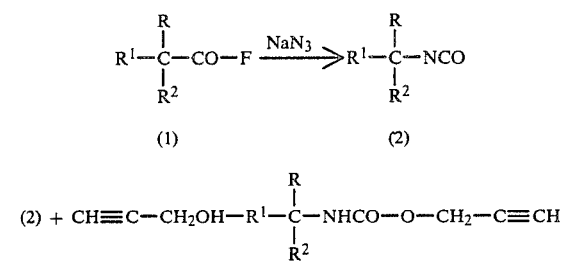

(wherein R, $R^1$ and $R^2$ have the abovementioned meaning).

The process according to the invention can be illustrated by the following preparation examples:

EXAMPLE 1

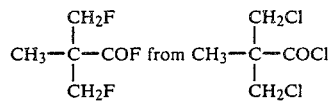

947.5 g (5 moles) of dichloropivaloyl chloride, 2 kg of tetramethylene sulphone and 1.16 kg (20 moles) of potassium fluoride are heated at 230° C. in a VA stirred autoclave under an initial pressure of 2 bar of $N_2$ for 5 hours and the mixture is cooled, let down and distilled under slightly reduced pressure. 576 g (79.2% of theory) of difluoropivaloyl fluoride (boiling point 110-120 mbar 52°-56° C.) are obtained. Yields of between 85 and 90% of theory are obtained on the 3 kg scale in a paddle reactor.

EXAMPLE 2

900 g (4 moles) of tris-chloromethylacetyl chloride (trichloropivaloyl chloride), 1.16 kg (20 moles) of potassium fluoride and 2,250 ml of tetramethylene sulphone are stirred at 200° C. under normal pressure for 5 hours, the mixture is cooled, 1 liter of xylene is added and the mixture is subjected to incipient distillation up to the boiling point of the tetramethylene sulphone. The xylene solution contains all the trisfluoromethylacetyl fluoride (80% of theory), which, because of its melting point of 50°-52° C. and the boiling point of 48° C./22 mbar and the high reactivity of the acid fluoride is generally further reacted directly in the solution.

EXAMPLE 3

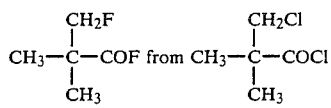

5.8 kg (100 moles) of potassium fluoride and 7.7 kg of tetramethylene sulphone are initially introduced into a 20 liter paddle reactor with distillation attachment and the mixture is subjected to incipient distillation at about 20 mbar, 10% of the solvent employed being taken off. The apparatus is gassed with $N_2$, the internal temperature is allowed to drop from 150° to 125°-130° C., 6.2 kg (40 moles) of chloropivaloyl chloride are sucked in and the apparatus is flushed with $N_2$ and sealed pressure-tight. After forcing in 3 bar of $N_2$, the mixture is warmed at 150° C. for 1 hour and at 230° C. for 12 hours, cooled to 80° C. and distilled under 100 mbar. 3.256 kg (68%) of fluoropivaloyl fluoride (boiling point 40°-41° C./100 mbar) and 1.4 kg (26% of chloropivaloyl fluoride (boiling point 65° C./100 mbar), as a by-product, are obtained. The result corresponds to a selectivity of 92% with 74% conversion.

The preparation of the synergistically active carbamic acid esters from the compounds of the formula (I) according to the invention via the isocyanates and subsequent reaction with an alcohol such as propargyl can be illustrated by the following example:

EXAMPLE 1 A 0-2-Propinyl N-(1,1-bis-fluoromethyl-ethyl)-carbamate

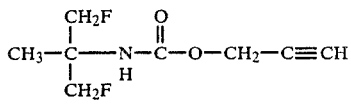

14 g (0.1 mole) of 2,2-bisfluoromethylpropionyl fluoride are dissolved in 200 ml of acetone. A solution of 6.5 g (0.1 mole) of sodium azide in 20 ml of water is added dropwise at 0° C. and the mixture is stirred at room temperature for 1 hour (about 20° C.). The aqueous phase is extracted twice with in each case 200 ml of toluene and the resulting toluene phase is washed twice with in each case 200 ml of water. After the toluene phase has been dried over sodium sulphate, it is heated slowly to 70°-80° C., until the evolution of gas which starts has ended. The mixture is then boiled under reflux for 1 hour. Completion of the formation of 1,1-bis-fluoromethylethyl isocyanate is monitored by IR spectroscopy (decrease $v_{CON_3}=2120$, increase $v_{N=C=O}=2250\,cm^{-1}$). 11.2 g of 2-propinyl alcohol are added drowpise to the resulting solution at about 20° C. and 10 mg of diazabicyclooctane (dabco) are added.

After the mixture has been heated to the boiling point for 4 hours, the reaction mixture is cooled and washed with water. After drying over sodium sulphate, the solvent is distilled off and the oil which remains is freed from residual solvent under a high vacuum. 13 g of 0-2-propinyl N-(1,1-bis-fluoromethyl-ethyl)-carbamate are obtained in the form of a colorless oil (68% of the theoretical yield) of $N_C^{20}$ 1.4430.

The remaining compounds of the formula (I) according to the invention can also be correspondingly converted into the carbamic acid ester synergistic agents:

$$R^1 - \underset{\underset{R^2}{|}}{\overset{\overset{R}{|}}{C}} - NH - COOCH_2 - C \equiv CH$$

| Example No. | R | $R^1$ | $R^2$ | Refractive index $n_D^{20}$ |
|---|---|---|---|---|
| 2A | $CH_2F$ | $CH_2F$ | $CH_2F$ | 1.4371 |
| 3A | $CH_2F$ | $CH_3$ | $CH_3$ | 1.4470 |

The surprising synergistic activity of the carbamic acid esters may be demonstrated with the aid of the following test results, the insecticidal active compound propoxur of the formula

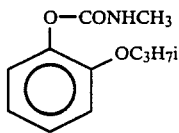  (A)

serving as the insecticidal component:

Test method used:

$LT_{100}$ test

Test insects: *Musca domestica* ♀♀, Weymanns strain (resistant)

Solvent: acetone

Solutions of the active compounds, synergistic agents and mixtures of active compounds and synergistic agents are prepared, and 2.5 ml thereof are pipetted onto filter paper discs 9.5 cm in diameter in Petri dishes. The filter paper absorbs the solutions. The Petri dishes remain uncovered until the solvent has evaporated completely. 25 test insects are then introduced into the Petri dishes and the dishes are covered with a glass lid.

The condition of the test insects is monitored continuously for up to 6 hours. The time required for a 100% knock-down effect is determined. If the $LT_{100}$ has not been reached after 6 hours, the percentage of knocked-down test insects is determined.

The active compounds, synergistic agents, concentrations of the active compounds, synergistic agents and mixtures and their actions can be seen from the following table.

Test results

| Active compound | Synergistic agent (Example No.) | Concentration in % | | $LT_{100}$ in minutes or at 360' in % |
|---|---|---|---|---|
| | | Active compound | Synergistic agent | |
| (A) | — | 1.0 | — | 360' = 60% |
| — | 1A | — | 0.2 | 360' = 20% |
| — | 2A | — | 0.2 | 360' = 90% |
| — | 3A | — | 0.2 | 360' = 20% |
| (A) | 1A | 0.04+ | 0.04 | 90' |
| (A) | 2A | 0.04+ | 0.04 | 90' |
| (A) | 3A | 0.04+ | 0.04 | 75' |

The pest-combating agents containing the synergistic agents can be used by the generally customary methods, for example in the form of sprays from wettable powders and the like.

It is understood that the specification and examples are illustrative but not limitative of the present invention and that other embodiments within the spirit and scope of the invention will suggest themselves to those skilled in the art.

We claim:

1. A compound of the formula

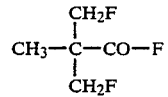

2. A compound of the formula

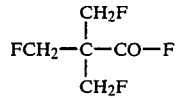

* * * * *